United States Patent [19]
Schafer et al.

[11] Patent Number: 4,605,431
[45] Date of Patent: Aug. 12, 1986

[54] COMPOSITIONS AND METHODS FOR REDUCING HERBICIDAL INJURY

[75] Inventors: David E. Schafer; Albert J. Czajkowski, both of Creve Coeur, Mo.

[73] Assignee: Monsanto Company, St. Louis, Mo.

[21] Appl. No.: 685,873

[22] Filed: Dec. 24, 1984

Related U.S. Application Data

[60] Continuation of Ser. No. 465,965, Feb. 14, 1983, Pat. No. 4,507,143, which is a division of Ser. No. 923,136, Jul. 10, 1978, Pat. No. 4,379,716, which is a continuation-in-part of Ser. No. 670,789, Mar. 26, 1976, abandoned.

[51] Int. Cl.⁴ .................... A01N 57/10; A01N 37/00
[52] U.S. Cl. ........................................ 71/87; 71/100; 71/118
[58] Field of Search ............................ 71/87, 100, 118

[56] References Cited

U.S. PATENT DOCUMENTS

| | | | |
|---|---|---|---|
| 3,131,509 | 5/1964 | Hoffmann | 71/77 |
| 3,989,503 | 11/1976 | Pallos et al. | 71/118 |
| 4,003,735 | 1/1977 | Czajkowski et al. | 71/118 |
| 4,036,628 | 7/1977 | Pallos et al. | 71/86 |
| 4,059,431 | 11/1977 | Takematsu et al. | 71/87 |
| 4,065,288 | 12/1977 | Hofer et al. | 71/87 |
| 4,379,716 | 4/1983 | Schafer et al. | 71/87 |
| 4,507,143 | 3/1985 | Schafer et al. | 71/87 |

FOREIGN PATENT DOCUMENTS 756980  4/1971  Belgium ................... 71/87

OTHER PUBLICATIONS

WOLCOTT, et al, "Effect of Structure on the Rate, etc." (1971) Tovicol & Appl. Pharm. 22, pp. 676–683 (1972).
HARMANN et al "Certain Thiolcarbamate Compounds", (1967), CA 67 No. 108272 w. (1967).
MONSANTO, "Esters of Thiolcarbamic Acid", (1961) CA 57, pp. 17977–17978 (1962).

Primary Examiner—Richard L. Raymond
Assistant Examiner—Raymond Covington
Attorney, Agent, or Firm—J. Timothy Keane; Paul D. Matukaitis

[57] ABSTRACT

The disclosure herein relates to the use of organophosphorous compounds as antidotes for thiolcarbamate herbicides used in various crops, particularly grass crops, e.g., corn, rice, barley, sorghum and wheat.

37 Claims, No Drawings

COMPOSITIONS AND METHODS FOR REDUCING HERBICIDAL INJURY

This is a continuation application of application Ser. No. 465,965 filed on Feb. 14, 1983, now U.S. Pat. No. 4,507,143, which is a divisional application of Ser. No. 923,136 filed on July 10, 1978, now U.S. Pat. No. 4,379,716, which is a continuation-in-part of application Ser. No. 670,789 filed on Mar. 26, 1976, abandoned.

BACKGROUND OF THE INVENTION

The invention herein pertains to the field of crop protection.

This invention relates to novel compositions and methods for reducing or nullifying injury to young crop plants by selective herbicides. More specifically, this invention relates to novel compositions and methods for reducing injury to young grass crop plants, e.g., corn, rice, barley, sorghum and wheat by thiolcarbamate herbicides, such as diallate and triallate, which comprises treating the habitat of the crop plant or the seed of the crop plant prior to planting, with an antidote for the selective herbicide.

Thiolcarbamate herbicides, such as diallate and triallate are very useful for controlling certain weeds in the presence of other growing plants. However, these herbicides sometimes injure certain crop plants, slowing growth and development at application rates necessary to stunt or kill the weeds. As a consequence, it is sometimes disadvantageous to employ thiolcarbamate herbicides to control weeds in the presence of certain crops, some of which are important commodities in the world food supply. Obviously, there is a need for a method of reducing or nullifying the injury of the crop plant by the selective herbicide while not affecting the herbicidal action on the weeds to be controlled.

DESCRIPTION OF THE PRIOR ART

It is known in the prior art to reduce herbicidal injury to various crops by use of antidotal or "safening" compounds which have an antagonistic or nullifying effect with respect to the active ingredients of the herbicide by one mechanism or another.

Illustrative of the use of antidotes for carbamate or thiolcarbamate herbicides in the prior art are U.S. Pat. No. 3,131,509 and South African Patent Publication No. 72/2519. U.S. Pat. No. 3,131,509 discloses the use of various hormone-type plant growth regulants, e.g., bromoalkyl compounds, as antagonists for certain carbamates. The South African patent discloses the use of various acetamide and carbamate compounds as antagonists for thiolcarbamate herbicides. U.S. Pat. No. 4,036,628 discloses the use of certain phosphate, phosphonate and phosphinate compounds as antidotes for certain thiolcarbamate herbicides. However, the reference does not suggest that organothiophosphorous compounds would have antidotal activity against thiolcarbamate herbicides.

There are, of course, many other compounds disclosed in the prior art as useful antidotes for carbamate and acetanilide herbicides. However, organophosphorous compounds do not seem to have been widely used as antidotes for thiolcarbamate herbicides. In most of the art relevant to use of organophosphorous compounds in agriculture the use has been as an insecticide, as a defoliant, as a herbicide, per se, or as a plant growth inhibitor of weeds or as fruit abscission agents. See, e.g., U.S. Pat. Nos. 3,879,189, 3,907,540, 3,861,899 and 3,826,640 as illustrative prior art for the use of organophosphorous compounds in crop protection uses.

SUMMARY OF THE INVENTION

The present invention relates to the use of certain organophosphorous compounds as antidotal, antagonistic or safening agents for reducing crop injury by thiolcarbamate herbicides. More particularly, this invention is primarily concerned with reducing injury to grass crops, e.g., barley, rice, sorghum and wheat, by the thiolcarbamate herbicides diallate or triallate.

Still more particularly, this invention relates to the use as antidotes for thiolcarbamate herbicides of organophosphorous compounds defined by the following formula

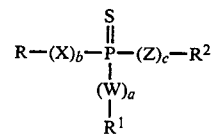

wherein a, b and c represent the integers zero or one, but cannot all be zero simultaneously;

W, X and Z independently represent oxygen or sulfur;

R, $R^1$ and $R^2$ independently represent hydrogen, $C_{1-13}$ alkyl, lower alkyl substituted lower alkyl, nitro lower alkyl, halo lower alkyl, lower alkenyl, halo lower alkenyl, lower alkynyl, halo lower alkylcarbonyl, halo lower alkenylsulfonyl lower alkyl, mono-lower alkyl amino, di-lower alkyl amino, halo lower alkenyl thio lower alkyl, lower mono- or di-alkyl aminocarbonyl lower alkyl, lower mono- or di-alkyl aminothiocarbonyl, halophenylthio, para-aminosulfonyl phenyl, para-nitrobenzoyl, halophenylthio lower alkyl, phenyl, benzyl, naphthyl, naphthyl substituted by one or two lower alkyl or halo moieties, α-nitromethylbenzyl, α-methylbenzyl, phenyl substituted by one to three $C_{1-13}$ alkyl, lower alkenyl, halo, $NO_2$, CN, $CF_3$ and $CH_3S$- moieties and no more than one of R, $R^1$ and $R^2$ can be quinolyl, 1-pyridinyl lower alkyl, 5-chlorothiophene-2-lower alkyl and N-lower alkyl di-lower alkyl anilino carbonyl lower alkyl; provided that when a is 0, c is 1 and Z is S, $R^2$ cannot equal hydrogen or halophenyl; phenyl cnanot be substituted with $NO_2$ and $CF_3$ simultaneously; when X and W are oxygen and Z is sulfur R, $R^1$ and $R^2$ cannot simultaneously equal $CH_3$; and when W, X and Z are oxygen R, $R^1$ and $R^2$ cannot simultaneously equal phenyl.

In the above formula the term "alkyl" refers to a straight or branched chain alkyl containing 1 to 13 carbon atoms. The preferred alkyls are those containing 1–6 carbon atoms. The term "lower alkyl" is used herein to refer to a straight or branched chain alkyl of from 1 to 6 carbon atoms, e.g., methyl, ethyl, propyl, isopropyl, n-butyl, isobutyl, sec-butyl, tert-butyl, n-pentyl, isopentyl, n-hexyl and the like. The term "halo" or halogen includes chlorine, bromine, fluorine and iodine atoms. The term "lower alkenyl" is used herein to refer to an alkenyl radical having from 2 to 6 carbon atoms, preferably from 3 to 5 carbons atoms. The term "lower alkynyl" is used herein to refer to an alkynyl radical having 2 to 6 carbon atoms, preferably 3 to 4 carbon atoms. The term "carbonyl" when used herein is understood to mean the

radical; the term "thiocarbonyl" refers to the radical

As will be described in more detail below, certain subclasses of organophosphorous compounds have exhibited a general pattern for degrees of effectiveness as antidotes for thiolcarbamate herbicides.

Other and interrelated aspects of this invention concern the provision of safened compositions comprising thiolcarbamate herbicides, especially diallate and triallate, and an effective amount of an organophosphorous antidote, and to methods of reducing injury to young crop plants, particularly grass crops such as barley, rice, sorghum and wheat by use of said safened compositions. The preferred crop plant to be safened is wheat.

The preferred specific embodiment of the invention includes the safening of, or reduction in injury to, wheat by triallate herbicide by use of the antidotal compound O,O-diethyl O-(m-tolyl)phosphorothioate.

The invention will be more clearly understood by reference to the following detailed description of specific embodiments thereof.

DETAILED DESCRIPTION OF THE INVENTION

Compounds which are useful in reducing or eliminating crop injury are referred to in the art variously as herbicidal antidotes, safeners or antagonistic agents. These compounds counteract the action of the herbicide to reduce injury to a given crop plant. In many instances weed injury is also reduced, but to tolerable levels which are determined by economic factors.

In the practice of the present invention, organophosphorous compounds within the above generic formula are used as antidotal compounds with thiolcarbamate herbicides. For exemplary purposes herein the thiolcarbamates will be represented by triallate and diallate. "Triallate" is the common name for the compound S-(2,3,3-trichloroallyl)-diisopropylthiolcarbamate; "diallate" is the common name for the compound S-(2,3-dichloroallyl)-diisopropylthiolcarbamate. Triallate and diallate are the active ingredients, respectively, in the herbicides Avadex BW ®, FAR-GO ® and Avadex ®, (registered trademarks of Monsanto Company).

In studies of a large number and variety of organophosphorous compounds tested, analyses of test results with particular applicability to triallate, have shown the following general pattern of effectiveness as antidotes of various classes of organophosphorous compounds:

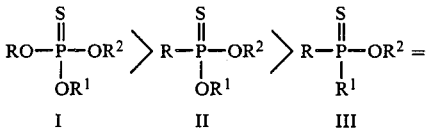

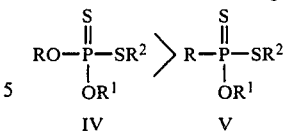

The compounds identified by structure in formulae I–V are known as: I, phosphorothioates, or thionophosphates; II, phosphonothioates; III, phosphinothioates; IV, phosphorodithioates and V, phosphonodithioates.

The amount of antidote employed in methods and compositions of this invention will vary according to the particular herbicide with which the agent is employed and the rate of application of the herbicide. In each instance the amount of antidote employed is an effective safening amount. By an effective safening amount is meant an amount which reduces crop injury by the herbicide. In the tests employed in illustrating this invention, the amount of crop injury was reduced by as much as 100 percent.

The compounds used herein as antidotes for thiolcarbamate herbicides are either known compounds or are readily prepared from known compounds by known and/or conventional methods of preparation.

The method and compositions of this invention are exemplified by the examples below.

EXAMPLES 1 THROUGH 92

The safening effectiveness of representative antidotes on triallate herbicide with respect to wheat is shown by the test results presented in Table I. For each antidote there is shown the antidote safening effect of the antidote in terms of reduction in percent crop injury. The "percent safening effect" is determined by the following calculation: [% inhibition of plant caused by herbicide alone + % inhibition of plant caused by antidote] − % inhibition of plant caused by herbicide/antidote combination. These results are obtained by the following procedure.

A good grade of top soil is placed in an aluminum pan and compacted to a depth of 9.5 to 12.7 mm. from the top of the pan. A predetermined number of seeds of each of the plant species to be tested are placed on top of the soil in the pans. A quantity of soil sufficient to substantially fill the pan is measured and placed in a suitable container. A measured quantity of the antidote compound dispersed or dissolved in a suitable carrier is sprayed on the soil in the container. A measured quantity of the triallate herbicide dispersed or dissolved in a suitable carrier is then sprayed on the soil in the container already treated with the safening agent. The quantity of triallate herbicide and antidote used is expressed in terms of kilograms per hectare. The soil containing the antidote and triallate herbicide is thoroughly mixed. The mixing is sometimes referred to as incorporation of the herbicide and antidote into the soil. The mixing or incorporation provides a substantially uniform distribution of the antidote and herbicide throughout the soil. The seeds are covered with the soil containing the antagonistic agent and triallate herbicide and the pans are leveled. The pans are then placed on a sand bench in the greenhouse and watered from below as needed. The plants are observed at the end of approximately 21 days and the results in terms of percent inhibition of each crop species are recorded. For each test series a pan of plants is also prepared containing no herbicide and no antidote as a control. Additionally, for each test, a pan of plants is prepared with soil covering the seed containing no triallate herbicide and only the measured amount of antidote being incorporated into the soil covering the seeds to ascertain any herbicidal effect of the antidote alone. For each series of tests the herbicidal effect of the triallate is observed from pans of plants treated with the same quantity of herbicide alone.

TABLE 1

| Example No. | Amount of Triallate (Kg/Ha) | Antidote Compound | Amount of Antidote (Kg/Ha) | Percent Safening Effect |
|---|---|---|---|---|
| 1 | 0.14 | O,O—Diethyl S—(methyl-2,6-xylylcarbamoylmethyl) phosphorodithioate | 8.96 | 55 |
| 2 | 0.28 | O—(2-Chloro-4-nitrophenyl) O,O—diethyl phosphorothioate | 4.48 | 20 |
| 3 | 0.28 | O—(3-Cyanophenyl) O,O—diethyl phosphorothioate | 8.96 | 70 |
| 4 | 0.28 | S—(3,3-Dichloroallyl) O,O—dimethyl phosphorodithioate | 8.96 | 40 |
| 5 | 0.28 | O—(3,3-Dichloroallyl) O,O—diethyl phosphorothioate | 4.48 | 35 |
| 6 | 0.28 | S—(3,3-Dichloroallyl) O,O—diethyl phosphorodithioate | 8.96 | 50 |
| 7 | 0.28 | O,O—Diethyl S—(1-methyl-2-nitroethyl) phosphorodithioate | 8.96 | 30 |
| 8 | 0.28 | S—(2,3-Dibromoallyl) O,O—diethyl phosphorodithioate | 4.48 | 30 |
| 9 | 0.28 | O,O—Diethyl O—(4-sulfamylphenyl) phosphorothioate | 8.96 | 80 |
| 10 | 0.28 | S—(3,3-Dichloroallylthiomethyl) O,O—diethyl phosphorodithioate | 8.96 | 60 |
| 11 | 0.28 | O,O—Diethyl-O—p-nitrophenyl phosphorothioate | 8.96 | 50 |
| 12 | 0.28 | O,O—Diethyl-O—p-nitrophenyl phosphorothioate | 8.96 | 60 |
| 13 | 0.28 | S—{[(p-chlorophenyl)thio]methyl}O,O—diethyl phosphorodithioate | 8.96 | 45 |
| 14 | 0.28 | O,O—Dimethyl O—[4-(methylthio)-m-tolyl] phosphorothioate | 4.48 | 85 |
| 15 | 0.28 | O,O—Dimethyl O—(4-nitro-m-tolyl) phosphorothioate | 4.48 | 20 |
| 16 | 0.28 | O,O—Dimethyl O—(2,4-5-trichlorophenyl) phosphorothioate | 4.48 | 35 |
| 17 | 0.28 | S[(3-chloro-2-butenyl sulfonyl)methyl] O,O—diethyl phosphorodithioate | 8.96 | 30 |
| 18 | 0.56 | S—(2-bromoallyl) O,O—diethylphosphorodithioate | 8.96 | 80 |
| 19 | 0.56 | S—(α-methyl benzyl) O,O—diethyl phosphorodithioate | 8.96 | 90 |
| 20 | 0.56 | O,O—Diethyl O(p-trifluoromethylphenyl) phosphorothioate | 8.96 | 95 |
| 21 | 0.28 | O,O—Diethyl S—(1-naphthylmethyl) phosphorodithioate | 8.96 | 20 |
| 22 | 0.28 | O,O—Diethyl S—2-propynyl phosphorodithioate | 8.96 | 45 |
| 23 | 0.28 | O,O,O—tributyl phosphorothioate | 8.96 | 55 |
| 24 | 0.28 | S—Chloroacetyl) O,O—diisopropylphosphorodithioate | 8.96 | 20 |
| 25 | 0.28 | S,S—(p-chlorophenyl)O,O—diisopropyl peroxy-phosphorotrithioate | 4.48 | 30 |
| 26 | 0.28 | O,O—Diisopropyl S,S—(O—nitrophenyl) peroxyphosphorotrithioate | 8.96 | 25 |
| 27 | 0.28 | Diethyldithiolcarbamic acid-O,O—diisopropyl S—hydrogen phosphorodithioate mixed anhydrosulfide | 4.48 | 50 |
| 28 | 0.28 | O,O—Diisopropyl S—[2-(2-pyridyl)ethyl] phosphorodithioate | 8.96 | 55 |
| 29 | 0.28 | S—[1-(ethoxycarbonyl)ethyl]O,O—diisopropyl phosphorodithioate | 8.96 | 40 |
| 30 | 0.42 | S—(5-Chloro-2-thienyl) O,O—diisopropylphosphorodithioate | 8.96 | 43 |
| 31 | 0.42 | O,O—Dipropyl S—hydrogen phosphorodithioate | 4.48 | 23 |
| 32 | 0.42 | S—(3,3-Dichloroallyl)O,O—diisopropyl phosphorodithioate | 4.48 | 97 |
| 33 | 0.42 | S—(3,3-Dichloroallyl)O,O—dipropyl phosphorodithioate | 8.96 | 92 |
| 34 | 0.42 | O,O—Dibutyl S—(3,3-dichloroallyl) phosphorodithioate | 8.96 | 22 |
| 35 | 0.42 | O,O—Dibutyl S—[α-(nitromethyl)benzyl] phosphorodithioate | 8.96 | 32 |
| 36 | 0.42 | O,O—Bis(2,4-dichlorophenyl) S—[α-(nitromethyl)benzyl] phosphorodithioate | 8.96 | 18 |
| 37 | 0.42 | O,O—Ditridecyl S—hydrogen phosphorodithioate (branched $C_{13}$) | 8.96 | 23 |
| 38 | 0.42 | O,O—Bis(p-dodecylphenyl) S—hydrogen phosphorodithioate (branched $C_{12}$) | 8.96 | 18 |
| 39 | 0.42 | O,O—Bis(2,4-dichlorophenyl) S—hydrogen phosphorodithioate-p-nitrothiolbenzoic acid mixed anhydro sulfide | 8.96 | 23 |
| 40 | 0.42 | S—[α-(nitromethyl)benzyl]O,O—diphenylphosphorodithioate | 8.96 | 18 |
| 41 | 0.28 | O—Methyl S—hydrogen phenyl phosphonodithioate | 4.48 | 35 |
| 42 | 0.28 | O—Phenyl N—isopropyl p-methylphosphonoamidothioate | 4.48 | 40 |
| 43 | 0.28 | O—(p-Chlorophenyl) N—isopropyl-p-methylphosphonoamidothioate | 4.48 | 20 |
| 44 | 0.28 | S—benzyl O—ethyl methylphosphonodithioate | 8.96 | 65 |
| 45 | 0.28 | O—(m-isopropylphenyl)-N—methyl methyl phosphonoamidothioate | 4.48 | 45 |
| 46 | 0.28 | O,O—diethyl-O—m-tolyl phosphorothioate | 8.96 | 80 |
| 47 | 0.28 | O—(3,3-Dichloroallyl)O—ethyl methylphosphonothioate | 8.96 | 50 |
| 48 | 0.28 | O—Ethyl O—(2,3,3-trichloroallyl) methylphosphonothioate | 8.96 | 35 |
| 49 | 0.28 | O—(2,3,3-Trichloroallyl) S—hydrogen methylphosphonodithioate | 1.12 | 50 |
| 50 | 0.28 | O—Butyl O—(3-trifluoromethylphenyl) methylphosphonothioate | 8.96 | 80 |
| 51 | 0.28 | O—(4-Cyano-3-trifluoromethylphenyl)O—n-propyl methylphosphonothioate | 8.96 | 30 |
| 52 | 0.28 | S—(N—methylcarbamoylmethyl)O—methyl phenylphosphonodithioate | 8.96 | 25 |
| 53 | 0.28 | S,S—diallyl methylphosphonotrithioate | 4.48 | 30 |
| 54 | 0.28 | O—(2,6-Dibromophenyl)O—ethyl methylphosphonothioate | 8.96 | 45 |
| 55 | 0.28 | O—(2-Chloroethyl)O—(4-cyanophenyl) isopropylphosphonothioate | 8.96 | 45 |
| 56 | 0.56 | O—(4-Chloro-m-tolyl)O—ethyl methylphosphonothioate | 4.48 | 45 |
| 57 | 0.56 | O—(o-Chlorophenyl)O—ethyl methylphosphonothioate | 8.96 | 95 |
| 58 | 0.56 | O—Ethyl N,N—diethyl P methylphosphonoamidothioate | 8.96 | 30 |
| 59 | 0.28 | O—Ethyl S—2-propynyl methylphosphonodithioate | 8.96 | 20 |
| 60 | 0.28 | S—(P—chlorophenylthiomethyl)O—isopropylmethylphosphonodithioate | 8.96 | 55 |
| 61 | 0.28 | O—(2-Allyl-6-chloro-phenyl)O—ethyl methylphosphonothioate | 8.96 | 70 |
| 62 | 0.28 | O—(4,6-Dichloro-m-tolyl)O—ethyl methylphosphonothioate | 8.96 | 45 |
| 63 | 0.14 | O—Ethyl O—(p-tolyl) methylphosphonothioate | 8.96 | 43 |
|  | 0.28 | O—Ethyl O—(p-tolyl) methylphosphonothioate | 8.96 | 80 |
| 64 | 0.28 | Methylphenylphosphinodithioic acid | 4.48 | 35 |
| 65 | 0.28 | O—Phenyl dimethylphosphinothioate | 8.96 | 40 |
|  | 0.14 | O—Phenyl dimethylphosphinothioate | 8.96 | 55 |
| 66 | 1.12 | O—(2,6-Xylyl) dimethylphosphinothioate | 8.96 | 23 |
|  | 0.56 | O—(2,6-Xylyl) dimethylphosphinothioate | 8.96 | 65 |
|  | 0.28 | O—(2,6-Xylyl) dimethylphosphinothioate | 8.96 | 70 |
|  | 0.14 | O—(2,6-Xylyl) dimethylphosphinothioate | 8.96 | 50 |

TABLE 1-continued

| Example No. | Amount of Triallate (Kg/Ha) | Antidote Compound | Amount of Antidote (Kg/Ha) | Percent Safening Effect |
|---|---|---|---|---|
| 67 | 0.28 | S—(2,4-Xylyl)dimethylphosphinodithioate | 8.96 | 30 |
| 68 | 0.28 | O—(2-Isopropyl-6-methyl-4-pyrimidynyl) dimethylphosphinothioate | 8.96 | 15 |
| 69 | 0.28 | O—(2,3,3-Trichloroallyl) dimethyl phosphinothioate | 8.96 | 30 |
| 70 | 0.28 | O—(2,4-Dichloro-1-naphthyl) dimethyl phosphinothioate | 8.96 | 40 |
| 71 | 0.28 | S—(2-Chloroallyl)O,O—diethyl phosphorothioate | 8.96 | 50 |
| 72 | 0.28 | S—(4-chlorophenyl S—phenyl methyl phosphonotrithioate | 8.96 | 15 |
| 73 | 0.56 | S—Hydrogen O,O—diethyl phosphorodithioate | 8.96 | 25 |
| 74 | 0.28 | O,O,O—triethyl phosphorothioate | 8.96 | 25 |
| 75 | 0.28 | O,O—dibutyl O—(p-nitrophenyl) phosphorothioate | 8.96 | 15 |

Further exemplification of the use of representative organophosphorous compounds as antidotes for thiolcarbamate herbicides is presented in Tables 2 and 3. In the tables the antidotal effect of various organophosphorous compounds is shown with the triallate in the grass crops barley, rice, sorghum and/or wheat. In these tests the herbicide/antidote was applied by incorporation in the soil. In Table 2 the expression "Δ Inhibition (%)" above the plants refers to the change in percent inhibition of plant growth resulting from treating the plants with a safened composition comprising the herbicide and the antidote vis-a-vis the percent inhibition of plant growth caused by the herbicide alone. The amount of said change in percent inhibition is expressed in plus (+) and minus (−) values representing, respectively, an increase or decrease in the percent inhibition resulting from the presence of the antidote.

TABLE 2

| Herbicide | Kg/Ha | Antidote | Rate Kg/Ha | ΔInhibition (%) Plant | | | |
|---|---|---|---|---|---|---|---|
| | | | | Barley | Rice | Sorghum | Wheat |
| Triallate | 0.28 | O,O—diethyl O—phenyl phosphorothioate | 4.48 | 0 | +15 | −55 | −55 |
| Triallate | 0.28 | O—(2,6-xylyl) dimethylphosphinothioate | 8.96 | 0 | +10 | −55 | −65 |
| Triallate | 0.28 | O—m-tolyl dimethylphosphinothioate | 8.96 | 0 | −55 | −40 | −10 |
| Triallate | 0.28 | O—methyl S—hydrogen phenyl phosphonodithioate | 4.48 | +10 | +25 | −15 | −35 |
| Triallate | 0.28 | S—benzyl O—ethyl methylphosphonodithioate | 8.96 | +10 | −55 | −65 | −65 |

Some effects resulting from variations in concentration of triallate herbicide at constant antidote concentration are shown in Table 3 for representative organophosphorous antidotes. The herbicide/antidote composition was applied by incorporation in the soil. An interesting observation to be noted in the date from these tests is that with most of the antidotes the herbicidal action of triallate in barley is decreased with increasing concentration of triallate, whereas the opposite effect is noted with certain exceptions, in sorghum and wheat.

TABLE 3

| Antidote | Rate (Kg/Ha) | Triallate (Kg/Ha) | ΔInhibition (%) PLANT | | |
|---|---|---|---|---|---|
| | | | Barley | Sorghum | Wheat |
| O—Phenyl dimethyl phosphinothioate | 8.96 | 1.12 | 0 | 0 | 0 |
| | | 0.56 | +5 | −3 | 0 |
| | | 0.28 | +10 | −8 | −40 |
| | | 0.14 | +10 | −65 | −55 |
| O—(2,6-xylyl) dimethylphosphinothioate | 8.96 | 1.12 | +15 | −38 | −23 |
| | | 0.56 | −5 | −63 | −65 |
| | | 0.28 | −10 | −68 | −70 |
| | | 0.14 | +10 | −65 | −50 |
| O—Methyl S—hydrogen phenyl phosphonodithioate | 4.48 | 1.12 | −10 | 0 | 0 |
| | | 0.56 | 0 | 0 | 0 |
| | | 0.28 | 0 | 0 | −50 |
| | | 0.14 | +25 | −65 | −45 |
| O—Phenyl N—isopropyl P—methyl phosphonoamidothioate | 4.48 | 1.12 | −30 | −53 | −3 |
| | | 0.56 | +15 | −88 | −50 |
| | | 0.28 | +10 | −88 | −60 |
| | | 0.14 | +20 | −90 | −65 |
| S—benzyl O—ethyl methylphosphonodithioate | 8.96 | 1.12 | −25 | −63 | |
| | | 0.56 | +10 | −73 | −85 |
| | | 0.28 | +20 | −73 | −90 |
| | | 0.14 | +10 | −70 | −65 |
| O,O—Diethyl S—(methyl-2,6-xylyl carbamoylmethyl) phosphorodithioate | 8.96 | 1.12 | −40 | 0 | 0 |
| | | 0.56 | −5 | 0 | −5 |
| | | 0.28 | 0 | −8 | −20 |
| | | 0.14 | +10 | −70 | −55 |

In a preferred embodiment of this invention the antidote compound is applied to the crop seed to reduce, minimize or eliminate crop injury by the herbicide.

In order to counteract injury by the herbicide, the crop seed need be treated with only a small amount of the antidote. For example, application rates of about 1100 g. to as low as about 1.5 g of antidote per bushel of seed may be used. The presently preferred application rate is in the range of about 1.5 g. to 550 g. of agent per bushel. The seed is treated with the antidote compound by use of conventional seed treating apparatus well known to the art. The seed is thoroughly mixed with the antidote in the seed treating apparatus, thereby giving a seed which is coated with the agent.

Since only a very small amount of antidote is required for the seed treatment, the compound may be formulated as a wettable powder or an emulsifiable concentrate which can be diluted with water by the seed treater for use in the seed treating apparatus. Alternatively, the antidote may be dissolved or suspended in an organic solvent for use as a seed treatment or the pure compound alone may be used under properly controlled conditions.

There are thus provided by this invention novel seed treating compositions containing one or more of the described active antidotes intimately dispersed in an inert carrier or diluent for the intended use. Such carriers may be either solid such as talc, clay, diatomaceous earth, sawdust, calcium carbonate, and the like or liquids such as water, kerosene, acetone, benzene, toluene, xylene, chlorinated hydrocarbons and the like in which the antidote may be either dissolved or dispersed. Emulsifying agents are advisably used to achieve a suitable emulsion if two immiscible liquids are used as a carrier. Wetting agents may also be used to aid in dispersing the active antagonistic agent in liquids used as a carrier in which the agent is not completely soluble. Emulsifying agents and wetting agents, also known as "surface active agents", are sold under numerous tradenames and may be either pure compounds, mixtures of compounds of the same general groups, or they may be mixtures of compounds of different classes. Typical satisfactory surface active agents which may be used are alkali metal higher alkylarylsulfonates such as sodium dodecylbenzenesulfonate and the sodium salts of alkylnaphthalesulfonic acids, fatty alcohol sulfates such as the sodium salts of monoesters of sulfuric acid with n-aliphatic alcohols containing 8–18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkali-casein compositions, long chain alcohols usually containing 10 to 18 carbon atoms, and condensation products of ethylene oxide with fatty acids, alkylphenols and mercaptans.

EXAMPLE 93

This example illustrates the safening effect of various organophosphorous compounds on thiolcarbamate herbicides in wheat when the antidote is applied as a seed treatment at varying concentrations.

The procedure used for the tests in this example was as follows:

Toluene solutions or suspensions of the antidote compounds were applied to wheat seeds to obtain the desired concentrations. Untreated weeds, e.g., wild oats (WO), downy brome grass (DB), blackgrass (BG) and green foxtail (FT), along with the treated and untreated wheat seeds, were planted in containers containing Ray silt loam soil. Soil cover layers were placed on the pre-seeded containers. In tests using the thiolcarbamate herbicide, e.g., triallate, the herbicide was applied to the soil cover layer with a belt sprayer and incorporated into the soil. The treated soil layers were then placed on the pre-seeded containers. The containers were then transferred to greenhouse benches and subirrigated through sand as needed. The results were observed about three weeks after initiation of the tests and tabulated in Table 4. In the table, a dash (—) indicates that the named weed species was not tested.

TABLE 4

| Herbicide | Amount of Herbicide Kg/Ha | Antidote Compound of Example No. | % Wheat Inhibition Treatment Conc. gm of Antidote/Kg of Seed | | | | % Inhibition Grass Weeds | | | |
|---|---|---|---|---|---|---|---|---|---|---|
| | | | 0 | .031 | .125 | .5 | DB | FT | BG | WO |
| Triallate | 0 | 46 | 0 | 10 | 10 | 15 | 0 | — | 0 | 0 |
| | 0.035 | | 0 | 0 | 0 | 15 | 60 | — | 20 | 90 |
| | 0.07 | | 10 | 0 | 10 | 15 | 100 | — | 80 | 95 |
| | 0.14 | | 45 | 0 | 0 | 10 | 100 | — | 90 | 100 |
| | 0.28 | | 65 | 0 | 0 | 10 | 100 | — | 98 | 95 |
| | 0.56 | | 98 | 70 | 0 | 10 | 100 | — | 98 | 100 |
| | 1.12 | | 98 | 80 | 15 | 15 | 100 | — | 100 | 100 |
| | 2.24 | | 98 | 98 | 60 | 25 | 100 | — | 100 | 100 |
| Triallate | 0 | 3 | 0 | 0 | 10 | 15 | 0 | — | 0 | 0 |
| | 0.035 | | 0 | 0 | 10 | 40 | 40 | — | 25 | 45 |
| | 0.07 | | 40 | 0 | 0 | 30 | 100 | — | 45 | 98 |
| | 0.14 | | 50 | 0 | 0 | 15 | 100 | — | 70 | 98 |
| | 0.28 | | 80 | 0 | 0 | 15 | 100 | — | 98 | 100 |
| | 0.56 | | 95 | 10 | 10 | 15 | 100 | — | 100 | 100 |
| | 1.12 | | 98 | 30 | 15 | 40 | 100 | — | 100 | 100 |
| | 2.24 | | 100 | 25 | 0 | 35 | 100 | — | 100 | 100 |
| Triallate | 0 | 10 | 0 | 0 | 20 | 0 | 0 | — | 0 | 0 |
| | 0.035 | | 0 | 0 | 10 | 20 | 20 | — | 10 | 90 |
| | 0.07 | | 0 | 0 | 0 | 20 | 80 | — | 75 | 98 |
| | 0.14 | | 20 | 0 | 10 | 15 | 98 | — | 80 | 95 |
| | 0.28 | | 80 | 10 | 10 | 30 | 100 | — | 98 | 95 |
| | 0.56 | | 80 | 25 | 25 | 30 | 100 | — | 98 | 100 |
| | 1.12 | | 95 | 80 | 70 | 40 | 100 | — | 100 | 100 |
| | 2.24 | | 100 | 90 | 85 | 70 | 100 | — | 100 | 100 |
| Triallate | 0 | 48 | 0 | 0 | 0 | 15 | 0 | — | 0 | 0 |
| | 0.035 | | 0 | 0 | 0 | 25 | 40 | — | 40 | 75 |
| | 0.07 | | 25 | 0 | 0 | 45 | 80 | — | 80 | 98 |
| | 0.14 | | 45 | 15 | 0 | 25 | 95 | — | 90 | 100 |
| | 0.28 | | 60 | 30 | 0 | 25 | 98 | — | 98 | 95 |
| | 0.56 | | 90 | 30 | 25 | 45 | 100 | — | 100 | 100 |
| | 1.12 | | 98 | 90 | 60 | 35 | 100 | — | 98 | 100 |
| | 2.24 | | 100 | 90 | 90 | 40 | 100 | — | 100 | 100 |
| Triallate | 0 | 50 | 0 | 10 | 10 | 30 | 0 | — | 0 | 0 |
| | 0.035 | | 0 | 0 | 0 | 60 | 20 | — | 30 | 50 |

TABLE 4-continued

| Herbicide | Amount of Herbicide Kg/Ha | Antidote Compound of Example No. | % Wheat Inhibition Treatment Conc. gm of Antidote/Kg of Seed | | | | % Inhibition Grass Weeds | | | |
|---|---|---|---|---|---|---|---|---|---|---|
| | | | 0 | .031 | .125 | .5 | DB | FT | BG | WO |
| | 0.07 | | 10 | 0 | 0 | 45 | 75 | — | 75 | 98 |
| | 0.14 | | 30 | 10 | 0 | 10 | 98 | — | 70 | 95 |
| | 0.28 | | 75 | 10 | 20 | 10 | 100 | — | 98 | 98 |
| | 0.56 | | 95 | 50 | 20 | 30 | 100 | — | 98 | 90 |
| | 1.12 | | 98 | 80 | 75 | 45 | 100 | — | 100 | 98 |
| ⊥ | 2.24 | ⊥ | 100 | 90 | 80 | 65 | 100 | — | 100 | 100 |
| Triallate | 0 | 54 | 0 | 0 | 0 | 10 | 0 | 0 | — | 0 |
| | 0.035 | | 0 | 0 | 0 | 15 | 60 | 0 | — | 85 |
| | 0.07 | | 0 | 0 | 0 | 15 | 80 | 30 | — | 95 |
| | 0.14 | | 35 | 0 | 0 | 15 | 95 | 20 | — | 100 |
| | 0.28 | | 60 | 0 | 0 | 20 | 100 | 40 | — | 100 |
| | 0.56 | | 90 | 45 | 10 | 30 | 100 | 60 | — | 100 |
| | 1.12 | | 98 | 75 | 25 | 20 | 100 | 80 | — | 100 |
| ⊥ | 2.24 | ⊥ | 100 | 80 | 70 | 55 | 100 | 85 | — | 100 |
| Triallate | 0 | 56 | 0 | 0 | 5 | 45 | 0 | 0 | — | 0 |
| | 0.35 | | 0 | 15 | 35 | 60 | 60 | 0 | — | 65 |
| | 0.07 | | 0 | 0 | 5 | 20 | 80 | 0 | — | 90 |
| | 0.14 | | 15 | 0 | 30 | 60 | 98 | 15 | — | 100 |
| | 0.28 | | 60 | 15 | 25 | 50 | 100 | 25 | — | 100 |
| | 0.56 | | 85 | 20 | 15 | 55 | 100 | 35 | — | 100 |
| | 1.12 | | 98 | 60 | 25 | 40 | 100 | 50 | — | 100 |
| ⊥ | 2.24 | ⊥ | 100 | 80 | 50 | 55 | 100 | 70 | — | 100 |
| Triallate | 0 | 57 | 0 | 0 | 0 | 55 | 0 | 0 | — | 0 |
| | 0.035 | | 0 | 0 | 0 | 50 | 80 | 0 | — | 95 |
| | 0.07 | | 0 | 0 | 0 | 65 | 95 | 0 | — | 100 |
| | 0.14 | | 0 | 15 | 0 | 65 | 100 | 10 | — | 100 |
| | 0.28 | | 60 | 0 | 0 | 60 | 100 | 25 | — | 100 |
| | 0.56 | | 70 | 20 | 15 | 70 | 100 | 35 | — | 100 |
| | 1.12 | | 90 | 30 | 30 | 75 | 100 | 45 | — | 100 |
| ⊥ | 2.24 | ⊥ | 95 | 55 | 40 | 60 | 100 | 70 | — | 100 |
| Triallate | 0 | 63 | 0 | 0 | 25 | 30 | 0 | 0 | — | 0 |
| | 0.035 | | 0 | 0 | 25 | 30 | 70 | 0 | — | 75 |
| | 0.07 | | 0 | 0 | 25 | 55 | 90 | 0 | — | 95 |
| | 0.14 | | 20 | 0 | 20 | 60 | 98 | 20 | — | 100 |
| | 0.28 | | 65 | 10 | 15 | 35 | 100 | 35 | — | 100 |
| | 0.56 | | 80 | 35 | 15 | 90 | 100 | 40 | — | 100 |
| | 1.12 | | 95 | 50 | 10 | 30 | 100 | 55 | — | 100 |
| ⊥ | 2.24 | ⊥ | 100 | 75 | 40 | 55 | 100 | 70 | — | 100 |

In addition to applying the herbicide/antidote safening composition by incorporating the components into the soil or by seed treatment with the antidote, it will be understood by those skilled in the art that any conventional alternative modes of application may be used. For example, the herbicide and antidote may be applied simultaneously, e.g., as a tank mix, or sequentially to the surface of the soil in which the seeds are planted prior to emergence of the plants or the herbicide and antidote may be applied postemergently after the plants have emerged. These alternative modes of application of herbicide and/or antidote are conventional practices in the crop protection art.

As indicated above in the section entitled "Detailed Description of the Invention", the organophosphorous compounds used as antidotes herein are all known and/or readily prepared by conventional processes as will be apparent to those skilled in the art. For example, typical methods of preparation, including alternatives, for preparing phosphates, phosphites, phosphorothioates (thionophosphates) or -dithioates, phosphonates, phosphonothioates and -dithioates, phosphinates and their sulfur analogs, and miscellaneous phosphorous compounds such as the amides, amines, etc., of phosphorous and phosphoric acids, e.g., phosphoroamidates, etc., are described in "Organophosphorous Compounds" by G. M. Kosolapoff, published by John Wiley and Sons, Inc., New York (1950) and in "Encyclopedia of Chemical Technology" (Edited by R. E. Kirk and D. F. Othmer), Vol. 10, pates 494–505 (1953); published by The Interscience Encyclopedia, Inc., New York.

While this invention has been described with respect to certain embodiments, it is to be understood that it is not so limited and that variations and modifications thereof obvious to those skilled in the art to which this invention appertains can be made without departing from the spirit or scope thereof.

We claim:

1. A method of reducing injury to crops by thiolcarbamate herbicides which comprises applying to the soil, crop or crop seed an effective safening amount of a compound of the formula

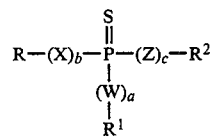

wherein
a, b and c represent the integers zero or one, but cannot all be zero simultaneously;
W, X and Z independently represent oxygen or sulfur;
R, R$^1$ and R$^2$ independently represent hydrogen, C$_{1-13}$ alkyl, lower alkyl substituted lower alkyl, nitro lower alkyl, halo lower alkyl, lower alkenyl, halo lower alkenyl, lower alkynyl, halo lower alkylcarbonyl, halo lower alkenylsulfonyl lower alkyl, mono-lower alkyl amino, di-lower alkyl amino, halo lower alkenyl thio lower alkyl, lower mono-or di-alkyl amino carbonyl lower alkyl, lower mono- or di-alkyl aminothiocarbonyl, halophenylthio, para-aminosulfonyl phenyl, para-nitrobenzoyl, halophenylthio lower alkyl, phenyl, benzyl, naphthyl, naphthyl substituted by one or two lower alkyl or halo moieties, α-nitromethylbenzyl, α-methylbenzyl, phenyl substituted by one to three $C_{1-13}$ alkyl, lower alkenyl, halo, $NO_2$, CN, $CF_3$ and $CH_3S$- moieties; and no more than one of R, $R^1$ and $R^2$ can be quinolyl, 1-pyridinyl lower alkyl, 5-chlorothiophene-2-lower alkyl and N-lower alkyl di-lower alkyl anilino carbonyl lower alkyl; provided that when a is zero, c is one and Z is sulfur, $R^2$ cannot equal hydrogen or halophenyl; phenyl cannot be substituted with $NO_2$ and $CF_3$ simultaneously; when X and W are oxygen and Z is sulfur R, $R^1$ and $R^2$ cannot simultaneously equal $CH_3$; and when W, X and Z are oxygen R, $R^1$ and $R^2$ cannot simultaneously equal phenyl.

2. A method of claim 1 wherein said crops are corn, barley, rice, sorghum and wheat.

3. A method of claim 2 wherein said crop is wheat and sorghum.

4. A method of claim 3 wherein said crop is wheat.

5. A method of claim 1 wherein in said compounds W, X and Z are oxygen and a, b and c are one.

6. A method of claim 1 wherein in said compounds W, X and Z are sulfur and a, b and c are one.

7. A method of claim 1 wherein in said compounds W and X are oxygen, Z is sulfur and a, b and c are one.

8. A method of claim 1 wherein in said compounds W is oxygen and X and Z are sulfur and a, b and c are one.

9. A method of claim 1 wherein in said compounds a and b are one and c is zero.

10. A method of claim 1 wherein in said compounds a and c are one and b is zero.

11. A method of claim 1 wherein in said compounds c and b are one and a is zero.

12. A method of claim 1 wherein in said compounds a is one and b and c are zero.

13. A method of claim 1 wherein in said compounds b is one and a and c are zero.

14. A method of claim 1 wherein in said compounds c is one and a and b are zero.

15. A method of claim 1 wherein in said compounds R, $R^1$ and $R^2$ are $C_{1-13}$ alkyl, lower alkyl substituted alkyl, nitro lower alkyl, halo lower alkyl, lower alkenyl, halo lower alkenyl and lower alkynyl.

16. A method of claim 1 wherein in said compounds R, $R^1$ and $R^2$ are phenyl, benzyl, naphthyl, α-nitromethylbenzyl, α-methyl benzyl and phenyl substituted by one to three $C_{1-13}$ alkyl, lower alkenyl, halo, $NO_2$, CN, $CF_3$ and methylthio moieties.

17. A method of claim 1 wherein the compounds are O,O-Diethyl O-(4-sulfamylphenyl)phosphorothioate, O,O-Dimethyl O-[4-(methylthio)-m-tolyl]phosphorothioate, S-(2-Bromoalkyl) O,O-diethyl phosphorodithioate, O,O-Diethyl O-(p-Trifluoromethylphenyl)phosphorothioate, S-(3,3-Dichloroalkyl) O,O-diisopropyl phosphorodithioate, O,O-Diethyl O-(m-tolyl)phosphorothioate, O-(o-Chlorophenyl) O-ethyl methylphosphonothioate, O-Ethyl O-(p-tolyl)methyl phosphonothioate.

18. A method of claim 17 wherein the compound is O,O-Diethyl O-(m-tolyl)phosphorothioate.

19. A method of claim 18 wherein said compound is applied to the seed.

20. A method of claim 1 wherein said compound is applied to the soil.

21. A method of claim 1 wherein said compound is applied to the soil and incorporated into the soil.

22. A method of claim 1 wherein said compound is applied to the seed.

23. A safened herbicide composition comprising a thiolcarbamate herbicide and an effective safening amount of a compound of the formula

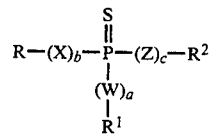

wherein
a, b and c represent the integers zero or one, but cannot all be zero simultaneously;
W, X and Z independently represent oxygen or sulfur;
R, $R^1$ and $R^2$ independently represent hydrogen, $C_{1-13}$ alkyl, lower alkyl substituted lower alkyl, nitro lower alkyl, halo lower alkyl, lower alkenyl, halo lower alkenyl, lower alkynyl, halo lower alkylcarbonyl, halo lower alkenylsulfonyl lower alkyl, mono-lower alkyl amino, di-lower alkyl amino, halo lower alkenyl thio lower alkyl, lower mono- or di-alkyl amino carbonyl lower alkyl, lower mono- or di-alkyl aminothiocarbonyl, halophenylthio, para-aminosulfonyl phenyl, para-nitrobenzoyl, halophenyl thio lower alkyl, phenyl, benzyl, naphthyl, naphthyl substituted by one or two lower alkyl or halo moieties, α-nitromethylbenzyl, α-methylbenzyl, phenyl substituted by one to three $C_{1-13}$ alkyl, lower alkenyl, halo, $NO_2$, CN, $CF_3$ and $CH_3S$-moieties; and no more than one of R, $R^1$ and $R^2$ can be quinolyl, 1-pyridinyl lower alkyl, 5-chlorothiophene-2-lower alkyl and N-lower alkyl di-lower alkyl anilino carbonyl lower alkyl; provided that when a is zero, c is one and Z is sulfur, $R^2$ cannot equal hydrogen or halophenyl; phenyl cannot be substituted with $NO_2$ and $CF_3$ simultaneously; when X and W are oxygen and Z is sulfur, R, $R^1$ and $R^2$ cannot simultaneously equal $CH_3$; and when W, X and Z are oxygen R, $R^1$ and $R^2$ cannot simultaneously equal phenyl.

24. A composition of claim 23 wherein in said antidote compounds W, X and Z are oxygen and a, b and c are one.

25. A composition of claim 23 wherein in said antidote compounds W, X and Z are sulfur and a, b and c are one.

26. A composition of claim 23 wherein in said antidote compounds W and X are oxygen, Z is sulfur and a, b and c are one.

27. A composition of claim 23 wherein in said compounds W is oxygen and X and Z are sulfur and a, b and c are one.

28. A composition of claim 23 wherein in said antidote compounds a and b are one and c is zero.

29. A composition of claim 23 wherein in said antidote compounds a and c are one and b is zero.

30. A composition of claim 23 wherein in said antidote compounds c and b are one and a is zero.

31. A composition of claim 23 wherein in said antidote compounds a is one and b and c are zero.

32. A composition of claim 23 wherein in said antidote compounds b is one and a and c are zero.

33. A composition of claim 23 wherein in said antidote compounds c is one and a and b are zero.

34. A composition of claim 23 wherein in said antidote compounds R, $R^1$ and $R^2$ are $C_{1-13}$ alkyl, lower alkyl substituted alkyl, nitro lower alkyl, halo lower alkyl, lower alkenyl, halo lower alkenyl and lower alkynyl.

35. A composition of claim 23 wherein in said antidote compounds R, $R^1$ and $R^2$ are phenyl, benzyl, naphthyl, α-nitromethylbenzyl, α-methyl benzyl and phenyl substituted by one to three $C_{1-13}$ alkyl, lower alkenyl, halo, $NO_2$, CN, $CF_3$ and methylthio moieties.

36. A composition of claim 23 wherein the compounds are O,O-Diethyl O-(4-sulfamylphenyl)phosphorothioate, O,O-Dimethyl O-[4-(methylthio)-m-tolyl]phosphorothioate, S-(2-Bromoalkyl) O,O-diethyl phosphorodithioate, O,O-Diethyl O-(p-Trifluoromethylphenyl)phosphorothioate, S-(3,3-Dichloroalkyl) O,O-diisopropyl phosphorodithioate, O,O-Diethyl O-(m-tolyl)phosphorothioate, O-(o-Chlorophenyl) O-ethyl methylphosphonothioate, O-Ethyl O-(p-tolyl)-methyl phosphonothioate.

37. A composition of claim 36 wherein the compound is O,O-Diethyl O-(m-tolyl)phosphorothioate.

* * * * *